(12) United States Patent
Wang et al.

(10) Patent No.: US 6,235,519 B1
(45) Date of Patent: May 22, 2001

(54) GENE INVOLVED IN THIOPHENE BIOTRANSFORMATION FROM NOCARDIA ASTEROIDES KGB1

(75) Inventors: Yongzhao Wang; John D. Childs; Charles H. Squires, all of The Woodlands, TX (US)

(73) Assignee: Energy Biosystems Corporation, The Woodlands, TX (US)

(*) Notice: Subject to any disclaimer, the term of this patent is extended or adjusted under 35 U.S.C. 154(b) by 0 days.

(21) Appl. No.: 09/030,995

(22) Filed: Feb. 26, 1998
(Under 37 CFR 1.47)

(51) Int. Cl.[7] .............................. C12N 1/14; C12N 9/02; C12N 1/20; C12N 15/00; C07H 21/04

(52) U.S. Cl. ................ 435/254.11; 435/189; 435/252.3; 435/262; 435/282; 435/320.1; 536/23.1; 536/23.2

(58) Field of Search ................................ 435/189, 252.3, 435/254.11, 320.1, 262, 282; 536/23.2, 23.1

(56) References Cited

U.S. PATENT DOCUMENTS

| | | | |
|---|---|---|---|
| 5,002,888 | 3/1991 | Kilbane, II | 435/252.31 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,297,625 | 3/1994 | Premuzic et al. | 166/246 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,870 | 10/1994 | Monticello et al. | 435/282 |

FOREIGN PATENT DOCUMENTS

WO 92/19700  11/1992  (WO).

OTHER PUBLICATIONS

Snell, E.E., "Tryptophanase: Structure, Catalytic Activities, and Mechanism of Action," *Adv. Enzymol.* 42:287–333 (1976).

Bibb, M.J., et al., "The Relationship between base composition and codon usage in bacterial genes and its use for the simple and reliable identification of protein–coding sequences," *Gene* 30:157–166 (1984).

Overby, L.H., et al., "Characterization of Flavin–Containing Monoxygenase 5 (FMO5) Cloned from Human and Guinea Pig: Evidence That the Unique Catalytic Properties of FMO5 Are Not Confined to the Rabbit Orthology," *Arch. Biochem. Biophys.* 317:275–284 (1995).

Chang, J H, et al., "Desulfurization of Diesel Oils by a Newly Isolated Dibenzothiophene–Degrading Nocardia sp. Strain CYKS2," *Biotechnology Progress* 14:851–855 (1998).

Atta–Asafo–Adjei, E., et al., "Dimethylaniline Monooxygenase (N–oxide Forming) 5 (EC 1.14.13.8) (Hepatic Flavin–containing Monooxygenase 5) (FMO 5) (Dimethylaniline Oxidase 5) (FMO 1C1) (FMO Form 3)," *J. Biol. Chem.* 268:9681–9689 (1993). Abstract.

*Primary Examiner*—Ponnathapu Achutamurthy
*Assistant Examiner*—Einar Stole
(74) *Attorney, Agent, or Firm*—Hamilton, Brook, Smith and Reynolds, P.C.

(57) ABSTRACT

The present invention relates to an isolated nucleic acid molecule which encodes one or more of the enzymes which catalyze one or more steps in the desulfurization of thiophene, or a homologue or active fragment thereof. The invention also includes a recombinant microorganism containing one or more such heterologous nucleic acid molecules. The invention also provides a method for desulfurizing a fossil fuel containing thiophene and/or one or more substituted thiophenes. The method comprises contacting the fossil fuel with an organism containing a recombinant nucleic acid molecule which encodes an enzyme which catalyzes the desulfurization of thiophene.

8 Claims, 7 Drawing Sheets

```
ATGAACAGGAGGGTAGCCGTCATCGGTGCTGGCCCATCGGGTCTTGCGCAATTGCGGGCATTCCAGTCTG      70
 M  N  R  R  V  A  V  I  G  A  G  P  S  G  L  A  Q  L  R  A  F  Q  S

CGGCGAGCAAAGGCGCCGACATCCCGGAGATCGTCTGCTTCGAGAAGCAGGCCAACTGGGGCGGGCTTTG     140
 A  A  S  K  G  A  D  I  P  E  I  V  C  F  E  K  Q  A  N  W  G  G  L  W

GAACTACACCTGGCGCACCGGTCTGGACCAGTATGGCGAGCCGGTCCATGGCTCGATGTACCGCTACCTG     210
  N  Y  T  W  R  T  G  L  D  Q  Y  G  E  P  V  H  G  S  M  Y  R  Y  L

TGGTCGAACGGCCCCAAGGAGGGGCTGGAGTTCGCCGACTACTCCTTCGAGGAGCATTTCGGCAAGCAGA    280
 W  S  N  G  P  K  E  G  L  E  F  A  D  Y  S  F  E  E  H  F  G  K  Q

TCGCCTCCTATCCGCCGCGCGCGGTCCTGTTCGACTACATCGAGGGCCGCGTGAACAAGGCAGGCGTGCG    350
 I  A  S  Y  P  P  R  A  V  L  F  D  Y  I  E  G  R  V  N  K  A  G  V  R

CGACTGGATCCGCTTCGAGAACGTCGTGCGCCTGGTGACCTGGGACGAGAACACCAGGAAGTTCACCGTC    420
  D  W  I  R  F  E  N  V  V  R  L  V  T  W  D  E  N  T  R  K  F  T  V

ACCGTCCAGGACCTGCCCAACGACCATTGCTATTCCGAAGATTTCGACAATGTGATCGTCGCCTCGGGCC    490
 T  V  Q  D  L  P  N  D  H  C  Y  S  E  D  F  D  N  V  I  V  A  S  G

ACTTCTCGACCCCGAACGTTCCCGAATTCCCGGGCTTCGACCAGTTCAACGGCCGCATCCTGCACGCCCA    560
 H  F  S  T  P  N  V  P  E  F  P  G  F  D  Q  F  N  G  R  I  L  H  A  H

TGACTTCCGCGACGCGCGCGAGTTCATCGGCAAGGACGTGCTGCTCATCGGCACCAGCTACTCGGCCGAG    630
  D  F  R  D  A  R  E  F  I  G  K  D  V  L  L  I  G  T  S  Y  S  A  E

GACATCGGCTCGCAATGCTGGAAATACGGCGCCAACTCCATCACCAACTGCTACCGCACCAAACCCATGG    700
 D  I  G  S  Q  C  W  K  Y  G  A  N  S  I  T  N  C  Y  R  T  K  P  M

GCTACCACTGGCCCGACAACTGGGAAGAAAAGCCGCTGCTGGAGAAGGTCCACGTCAACACCGCCACCTT    770
 G  Y  H  W  P  D  N  W  E  E  K  P  L  L  E  K  V  H  V  N  T  A  T  F

CAAGGACGGCTCGACCAAGCAGATCGACGCCATCATCCTGTGCACCGGCTACAAGCACCATTTCCCCTTC    840
  K  D  G  S  T  K  Q  I  D  A  I  I  L  C  T  G  Y  K  H  H  F  P  F

CTGCCCGACGACCTGCGCCTGAGGACGGCCAACCGCCTGGCGACGGCCGATCTCTACAAGGGCGTCGCCT    910
 L  P  D  D  L  R  L  R  T  A  N  R  L  A  T  A  D  L  Y  K  G  V  A

ATGTCCACAATCCGGCGCTGTTCTACATCGGCATGCAGGACCAGTGGTTCACCTTCAACATGTTCGACGC    980
 Y  V  H  N  P  A  L  F  Y  I  G  M  Q  D  Q  W  F  T  F  N  M  F  D  A

CCAGGCCTGGTGGGCGCGCGACGTGATCCTGGGCCGCATCGCCCTGCCCGCGGGCAAGCAGGAGATGGTC   1050
  Q  A  W  W  A  R  D  V  I  L  G  R  I  A  L  P  A  G  K  Q  E  M  V

GCCGATGTCGAGGCCCGCGTCGCCGCCGAGGACGCCGGCAAGGACGACTACGACGCGATCCGCTATCAGG   1120
 A  D  V  E  A  R  V  A  A  E  D  A  G  K  D  D  Y  D  A  I  R  Y  Q

GCGACTACGTCAAGGAGCTGATCGCCGAGACCGACTATCCGAGCTTCGACGTCGACGGCGCCAACGAAGC   1190
 G  D  Y  V  K  E  L  I  A  E  T  D  Y  P  S  F  D  V  D  G  A  N  E  A

CTTCTTCGAGTGGAAGAAGCACAAGAAGAAGAACATCATGGAGTTCCGCCACAACTCCTATCGCTCGGTC   1260
  F  F  E  W  K  K  H  K  K  K  N  I  M  E  F  R  H  N  S  Y  R  S  V

ATCACCGGCACCATGGGCCCGCCCCACCACACGCCCTGGAAGGATGCCCTCGACGATTCGCTGCAAGCCT   1330
 I  T  G  T  M  G  P  P  H  H  T  P  W  K  D  A  L  D  D  S  L  Q  A

ATCTCGGCACACAGGCCGCACCAGCCGCAGCAGAA                                      1365
 Y  L  G  T  Q  A  A  P  A  A  A  E
```

Fig. 1

```
ORF1    MNRRVAVIGAGPSGLAQLRAFQSAASKGADIPEIVCFEKQANWGGLWNYT           50
        .:|:||||:|.|||.  ::.          ..: | ||||: .: ||||.:
FMO5    TKKRIAVIGGGVSGLSSIKCC......VEEGLEPVCFERTDDIGGLWRF.           43

ORF1    WRTGLDQYGEPVHGSMYRYLWSNGPKEGLEFADYSFEEHFGKQIASYPPR          100
        :: .|..::|:|: :  |..||  : |.||.:.:|:     :.:  ..
FMO5    .....QENPEEGRASIYKSVIINTSKEMMCFSDYPIPDHY....PNFMHN           84

ORF1    AVLFDYIEGRVNKAGVRDWIRFENVVRLVTWDEN...TRKFTVTVQDLPN          147
        | :::|:    ...  :: .:|||...|  |...:.  ..:.|...:. ..
FMO5    AQVLEYFRMYAKEFDLLKYIRFKTTVCSVKKQPDFATSGQWEVVTESEGK          134

ORF1    DHCYSEDFDNVIVASGHFSTPNVP..EFPGFDQFNGRILHAHDFRDAREF          195
        ..   : ||.|:|..||  ..::|  .|||::.|.|...|..|:::: :|
FMO5    KE..MNVFDGVMVCTGHHTNAHLPLESFPGIEKFKGQYFHSRDYKNPEGF          182

ORF1    IGKDVLLIGTSYSAEDIGSQ..............................          215
        .||  |::||.|.:  |::|::: :
FMO5    TGKRVIIIGIGNSGGDLAVEISQTAKQVFLSTRRGAWILNRVGDYGYPAD          232

ORF1    ..........CWKYGANSITNCYRTKPMGYHWPDN.WEEKPL........          246
                  .||..:.|:.|  | .|.:.  ::...: :: ||
FMO5    VLFSSRLTHFIWKICGQSLANKYLEKKINQRFDHEMFGLKPKHRALSQHP          282

ORF1    .............LEKVHVN.......TATFKDGS.TKQIDAIILCTGYK          275
                     | |||..|       .|.|.|||   :|||:|:.|||.
FMO5    TLNDDLPNRIISGLVKVKGNVKEFTETAAIFEDGSREDDIDAVIFATGYS          332

ORF1    HHFPFLPDDLRLRTANRLATADLYKGV..AYVHNPALFYIGMQDQWFTF.          322
        .||||.|.::: ...    .|||  |   : ..|.| .||: :..:   .:
FMO5    FDFPFLEDSVKVVKNK....ISLYKKVFPPNLERPTLAIIGLIQPLGAIM          378

ORF1    NMFDAQAWWARDVILGRIALPAGKQEMVADVEARVAAEDAGKDDYDAIRY          372
        : : |::||  :|: |  .|| :. ||:|::.       |.|: :|   .   |.
FMO5    PISELQGRWATQVFKGLKTLP.SQSEMMAEISK..AQEEIDKRYVESQRH          425

ORF1    ..QGDYVKELIAETDYPSFDVDGANEAFFEWKKHKKKNIMEFRHNSYRSV          420
          ||||:...: ..     |: |....::.:      ..|  :.: ..:  .:
FMO5    TIQGDYIDTMEELA.....DLVGVRPNLLSLAFTDPKLALHLLLGPCTPI          470

ORF1    ITGTMGPPH.HTPWKDAL..DDSLQAYLGTQAAPAAAE............          455
        . ||..  ..::|. |   ||.|.:   | |....  ...
FMO5    HYRVQGPGKWDGARKAILTTDDRIRKPLMTRVVERSSSMTSTMTIGKFML          520
```

Fig. 7

GENE INVOLVED IN THIOPHENE BIOTRANSFORMATION FROM NOCARDIA ASTEROIDES KGB1

BACKGROUND OF THE INVENTION

Organic sulfur in fossil fuels causes environmental pollution when combusted and sulfur in petroleum can affect the performance of the refining equipment. High levels of sulfur in gasoline can also deactivate catalyst-based engine exhaust emission control systems (Gonzalez, R. G., Hart's Fuel Technology and Management, November/December 1996, 56–61). Therefore, low sulfur level gasoline is required by government regulation and desired by the refinery and auto industry.

Many biocatalysts and processes have been developed to desulfurize fossil fuels, including those described in U.S. Pat. Nos. 5,356,801, 5,358,870, 5,358,813, 5,198,341, 5,132,219, 5,344,778, 5,104,801 and 5,002,888, incorporated herein by reference. Analyses indicate that a limitation in the commercialization of the technology is the ability of the biocatalysts, such as the bacteria and enzymes that are involved in the desulfurization process, to catabolize or metabolize only specific types of organosulfur compounds. These organosulfur compounds, contain aromatic rings, such as, for example, dibenzothiophene (DBT). Often, other organosulfur compounds, such as thiophene, 2,2'-bithiophene, 2-methylthiophene and 3-methylthiophene, remain in the refined fossil fuel without significant removal by the biocatalyst.

The most common method for petroleum desulfurization is hydrotreating. However, with increasingly stringent regulations this is becoming more difficult and expensive. Conventional hydrotreating can decrease the sulfur level in FCC gasoline from 1000–2000 parts per million (ppm) to 200 ppm for a relatively low cost. However, it is very expensive to produce FCC gasoline below the 200 ppm specification because the light fraction of the FCC gasoline must also be hydrotreated. Due to the high olefin content of the light fraction, the hydrotreating process involves much higher hydrogen consumption and octane loss due to the saturation of olefins (Gonzalez, R. G. (1996), supra).

Over 90% of the sulfur in gasoline resulting from fluid catalytic cracking occurs in thiophene and substituted thiophenes. Thus, to obtain gasoline meeting current requirements for low sulfur content, methods are needed for removing a substantial amount of the thiophene and substituted thiophenes present in gasoline. Therefore, a need exists for efficient and economical methods for removing thiophene and substituted thiophenes from gasoline.

SUMMARY OF THE INVENTION

The present invention relates to the cloning and characterization of genes from *Nocardia asteroides* strain KGB1 which encode one or more enzymes which catalyze the biotransformation of thiophene and substituted thiophenes.

In one embodiment, the invention includes an isolated nucleic acid molecule, such as a DNA or RNA nucleotide sequence or molecule, which encodes one or more enzymes which catalyze one or more steps in the desulfurization of thiophene. Suitable nucleotide sequences can be isolated from, for example, *Nocardia asteroides* strain KGB1.

The present invention also provides a recombinant non-human organism which contains a heterologous nucleic acid molecule comprising a nucleotide sequence encoding one or more enzymes which catalyze the desulfurization of thiophene. In one embodiment, the nucleotide sequence which encodes the desulfurization enzyme(s) is derived from a Nocardia organism, such as *Nocardia asteroides* strain KGB1.

In a further embodiment, the invention provides a method of desulfurizing a fossil fuel, which comprises thiophene or a substituted thiophene. The method includes the steps of (1) contacting the fossil fuel with an aqueous phase containing a recombinant biocatalyst which contains a heterologous nucleic acid molecule comprising a nucleotide sequence encoding one or more enzymes which catalyze the desulfurization of thiophene, thereby forming a fossil fuel and aqueous phase mixture; (2) maintaining the mixture under conditions sufficient for biocatalysis, thereby resulting in a fossil fuel having a reduced thiophenic sulfur content; and (3) separating the fossil fuel having a reduced thiophenic sulfur content from the resulting aqueous phase.

BRIEF DESCRIPTION OF THE DRAWINGS

FIG. 1 sets forth the nucleotide sequence (SEQ ID NO: 1) and the corresponding amino acid sequence (SEQ ID NO: 2) of the open reading frame involved in biotransformation of thiophenes from *Nocardia asteroides* strain KGB1.

FIG. 7 presents a comparison of the amino acid sequence set forth in SEQ ID NO: 2 and the sequence of human FMO5 (dimethylaniline monooxygenase (N-oxide forming) flavin monooxygenase).

DETAILED DESCRIPTION OF THE INVENTION

Figure 2A:
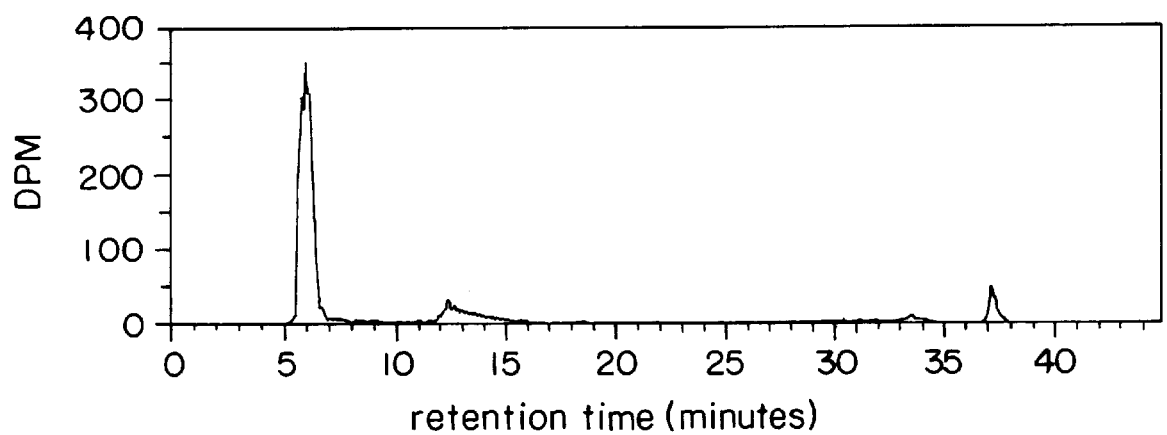
FIG. 2A presents the results of $^{14}$C-thiophene biotransformation by KGB1 cells grown on benzothiophene as sulfur source.

The features and other details of the invention will now be more particularly described and pointed out in the claims. It will be understood that the particular embodiments of the invention are shown by way of illustration and not as limitations of the invention. The principal features of this invention can be employed in various embodiments without departing from the scope of the invention.

Sulfur-bearing heterocycles are known to be stable to conventional desulfurization treatments, such as hydrodesulfurization (HDS). For this reason, they are said to be refractory or recalcitrant to HDS treatment. Thus, much of the residual post-HDS organic sulfur in refined petroleum products, such as gasoline and naphtha, occurs in sulfur heterocyclic compounds, such as thiophene and substituted thiophenes, for example, thiophene derivatives which are substituted by one or more substituted or unsubstituted alkyl or aryl groups.

The terms "thiophene" and "substituted thiophene", as used herein, refer to thiophenic compounds, optionally having one or more substituents attached to the thiophene ring. This term is not intended to include complex fused ring systems comprising a thiophenic ring (e.g. dibenzothiophene). For example, the thiophene substituent(s) can be, independently, alkyl, alkenyl, haloalkyl, alkoxylalkyl, aryl, alkoxy, halo, amino, nitro, alkyl- or arylcarbonyl, carboxyl, aminocarbonyl, alkoxycarbonyl, etc. The alkyl or alkenyl group can be straight chain, branched or cyclic and can contain between 1 to about 8 carbons, for example, and include methyl, ethyl, ethenyl, propyl, propenyl, isopropyl, etc. Representative substituted thiophenes include 2-methylthiophene and 3-methylthiophene.

The term "thiophenic sulfur" refers to sulfur which is present as a component of thiophene or a substituted thiophene.

The term "aryl group," as used herein, includes aromatic carbocyclic and heterocyclic rings. Examples of suitable carbocyclic aryl groups include phenyl, naphthyl, tetrahydronaphthyl, anthracene and substituted derivatives thereof. Examples of suitable heterocyclic aryl groups include thiophenyl, benzothiophenyl, benzofuranyl, pyridinyl, quinolino and substituted derivatives thereof. In a particular embodiment, the thiophene derivative is 2,2'-bithiophene or a substituted 2,2'-bithiophene. Suitable substituents include those listed above.

The present invention relates to the isolation of a microorganism capable of using thiophene and substituted thiophenes as a sole source of sulfur and the cloning of genes from this organism which encode one or more enzymes which catalyze the desulfurization of thiophene and substituted thiophenes.

*Nocardia asteroides* strain KGB1 was isolated from soil samples through an enrichment method using benzothiophene as the sole sulfur source, as described in copending application Ser. No. 09/031,005, the contents of which are incorporated by reference herein in their entirety. This microorganism was also able to grow on thiophenes, such as 3-methyl-thiophene, as the sole sulfur source. KGB1 was identified as a strain of *Nocardia asteroides* based on fatty acid analysis. A sample of this microorganism was deposited with the American Type Culture Collection, Rockville, Md., under the terms of the Budapest Treaty and assigned deposit no. ATCC 202089.

When grown on benzothiophene as the sole source of sulfur, KGB1 is able to convert indole to indigo. However, KGB1 grown on a sulfate-containing medium lacks this ability, suggesting that expression of an enzyme or enzymes involved in the conversion of indole to indigo is repressed by sulfate. Further, when grown on sulfate, KGB1 was unable to desulfurize $^{14}$C-thiophene, suggesting that the same enzyme or enzymes are involved in both thiophene desulfurization and the conversion of indole to indigo. This possibility provided a strategy for identifying clones containing the corresponding genes as the production of indigo results in a deep blue color.

The production and examination of clones containing portions of the genomic DNA of KGB1 are described in Examples 2 and 3. The gene encoding thiophene desulfurization activity was localized to a 2.4 kb PstI fragment. This nucleotide sequence comprises an open reading frame, referred to hereinafter as "ORF". ORF encodes a 455 amino acid protein with a calculated molecular weight of 51,800.

In one embodiment, the present invention provides an isolated nucleic acid molecule that encodes an enzyme which catalyzes one or more steps in the desulfurization of thiophene and/or substituted thiophenes. The isolated nucleic acid molecule can be, for example, a polynucleotide sequence, such as deoxyribonucleic acid (DNA) sequence or a ribonucleic acid (RNA) sequence. The isolated nucleic acid molecules of the invention include molecules comprising the nucleotide sequence depicted in FIG. 1 (SEQ. ID NO: 1).

In another embodiment, the invention includes an isolated nucleic acid molecule comprising a nucleotide sequence which is substantially the same as, or homologous to, the sequence of SEQ ID NO: 1 or the complement thereof. Such a nucleotide sequence exhibits at least about 80% homology, or sequence identity, with the sequence of SEQ ID NO: 1, preferably at least about 90% homology or sequence identity. Particularly preferred sequences have at least about 95% homology to or have substantially the same sequence as SEQ ID NO: 1. Preparation of mutant nucleotide sequences can be accomplished by methods known in the art as are described in Old, et al., *Principles of Gene Manipulation*, Fourth Edition, Blackwell Scientific Publications (1989), in Sambrook et al., and in Ausubel et al.

The invention further includes nucleic acid molecules which are useful as hybridization probes, for example, for the isolation of the genes from *Nocardia asteroides* KGB1 encoding desulfurization enzymes or identical or homologous genes from other organisms. Such molecules comprise nucleotide sequences which hybridize to all or a portion of the nucleotide sequence of SEQ ID NO.: 1 or to non-coding regions immediately (within about 1000 nucleotides) 5' or 3' of each open reading frame. The invention also includes an isolated nucleic acid molecule which comprises a fragment of the nucleotide sequence set forth in SEQ ID NO.: 1 or the complement of one of this sequence. Such a fragment will generally comprise at least about 20 or at least about 40 contiguous nucleotides and, preferably, at least about 50 contiguous nucleotides of one of the disclosed sequences. Preferably, the hybridization probe of the invention hybridizes to the sequence set forth in SEQ ID NO: 1 under stringent conditions, such as those set forth by Sambrook et al. and Ausubel et al. For example, under conditions of high stringency, such as high temperatures and low salt concentrations, only DNA molecules which are essentially exact matches, or complements, will hybridize, particularly if the probe is relatively short. Hybridization under conditions of lower stringency, such as low temperatures, low formamide concentrations and high salt concentrations, allows greater mismatch between the probe and the target DNA molecule. It is particularly preferred that the nucleic acid molecule hybridizes selectively to the disclosed sequence.

The nucleic acid molecules of the invention can be synthesized chemically from the disclosed sequence. Alternatively, the nucleic acid molecules can be isolated from a suitable nucleic acid library (such as a DNA library) obtained from a microorganism which is believed to possess the nucleic acid molecule (such as *Nocardia asteroides* sp. strain KGB1), employing hybridizing primers and/or probes designed from the disclosed sequences. Such a method can result in isolating the disclosed molecules (or spontaneous mutants thereof) for use in preparing recombinant enzymes, confirming the disclosed sequences, or for use in mutagenizing the native sequences.

In yet another embodiment, the nucleic acid molecule of the present invention is a nucleic acid molecule, such as a recombinant DNA molecule, resulting from the insertion into its chain by chemical or biological means, of one or more of the nucleotide sequences described above. Recombinant DNA includes any DNA synthesized by procedures using restriction nucleases, nucleic acid hybridization, DNA cloning, DNA synthesis or any combination of the preceding. Methods of construction can be found in Sambrook et al. and Ausubel et al., and additional methods are known by those skilled in the art.

The nucleic acid molecules of the invention further include nucleic acid molecules comprising a nucleotide sequence which encodes the amino acid sequence set forth in SEQ ID NO: 2. The invention also includes an isolated nucleic acid molecule comprising a nucleotide sequence which encodes an amino acid sequence which is substantially the same as SEQ ID NO: 2. Such an amino acid sequence exhibits at least about 80% homology or sequence identity with SEQ ID NO: 2, preferably at least about 90% homology. Particularly preferred sequences have at least about 95% homology or have substantially the same sequence.

The recombinant DNA molecule or fragment thereof of the present invention is intended to encompass any DNA resulting from the insertion into its chain, by chemical or biological means, of one or more genes encoding a biocatalyst capable of selectively cleaving thiophenic carbon-sulfur bonds, said gene not originally present in that chain. Recombinant DNA includes any DNA created by procedures using restriction nucleases, nucleic acid hybridization, DNA cloning, DNA sequencing or any combination of the preceding. Methods of construction are known in the art and can be found, for example, in Sambrook et al.

Procedures for the construction of the DNA plasmids or vectors of the present invention include those described in Sambrook et al., supra, and other methods known by those skilled in the art. The terms "DNA plasmid" and "vector" are intended to encompass any replication competent plasmid or vector capable of having foreign or exogenous DNA inserted into it by chemical or biological means and subsequently, when transfected into an appropriate non-human host organism, of expressing the product of the foreign or exogenous DNA insert (i.e., of expressing the biocatalyst of the present invention). In addition, the plasmid or vector must be receptive to the insertion of a nucleic acid molecule or fragment thereof of the invention, said nucleic acid molecule encoding a biocatalyst that catalyzes one or more steps in the desulfurization of thiophene. Within the plasmid, the nucleic acid molecule of the invention is, optionally, operatively linked to a promoter. Procedures for the construction of DNA plasmid vectors include those described, for example, in Sambrook et al., supra.

The invention also includes an enzyme having the amino acid sequence of SEQ ID NO: 2, which is encoded by the nucleotide sequence set forth in SEQ ID NO: 1. The invention also includes enzymatically active fragments of the enzyme of SEQ ID NO: 2 and enzymes having amino acid sequences homologous to SEQ ID NO: 2, such as, for example, enzymatically active mutants of the protein set forth in SEQ ID NO: 2. As used herein, the term "homologous" describes a protein having at least 80%, preferably 90%, sequence identity or homology with the protein set forth in SEQ ID NO: 2. The homologous proteins described herein can be native to an organism, such as a microorganism, for example, *Nocardia asteroides* strain KGB1 and mutants thereof. In one embodiment, the enzyme is a recombinant protein and results from expression of a heterologous nucleic acid molecule in a host organism. The homologous proteins of the invention can also be non-naturally occurring. For example, a homologous enzyme can be a mutant thiophene biotransformation enzyme which has a modified amino acid sequence resulting from insertion, deletion or substitution of one or more amino acids in the amino acid sequence set forth in SEQ ID NO: 2. Such amino acid sequence variants can be prepared by methods known in the art, such as site-directed mutagenesis and random mutagenesis. In one embodiment, the enzyme has the sequence set forth in SEQ ID NO: 2 or a sequence homologous thereto and is free of other Nocardia proteins.

In another embodiment, the invention relates to a recombinant or transformed non-human host organism which contains a heterologous DNA molecule of the invention, as described above. The recombinant non-human host organism can be created using any method for introducing a recombinant plasmid, such as a plasmid of the invention described above, into the organism of choice, such as transformation, conjugation, and electroporation. By the term "non-human host organism" is intended any non-human organism capable of uptake and expression of foreign recombinant DNA. Suitable non-human host organisms include bacteria, such as Pseudomonads, *E. coli*, Rhodococcus and Sphingomonas species.

The recombinant organism can be derived from a host organism which does not contain native genes encoding a biodesulfurization catalyst. Such an organism can be, for example, a bacterium which is a species of Pseudomonas. The recombinant organism can also be derived from a host organism which contains native genes encoding a biodesulfurization catalyst, such as a catalyst capable of selectively cleaving the carbon-sulfur bonds of dibenzothiophene or a biocatalyst capable of desulfurizing thiophene. Genes encoding a biocatalyst capable of selectively desulfurizing dibenzothiophene are disclosed in U.S. Pat. No. 5,356,801 and U.S. patent application Ser. No. 08/851,089, each of which is incorporated herein by reference. Recombinant organisms containing such genes are disclosed in U.S. patent application Ser. No. 08/851,088, incorporated herein by reference.

In a further embodiment, the invention provides a method of desulfurizing a fossil fuel, which comprises thiophene or a substituted thiophene. The method includes the steps of (1) contacting the fossil fuel with an aqueous phase containing a recombinant biocatalyst which contains a heterologous nucleic acid molecule comprising at least one heterologous enzyme which catalyzes at least one step in the desulfurization of thiophene, thereby forming a fossil fuel and aqueous phase mixture; (2) maintaining the mixture under conditions sufficient for biocatalysis, thereby resulting in a fossil fuel having a reduced thiophenic sulfur content; and (3) separating the fossil fuel having a reduced thiophenic sulfur content from the resulting aqueous phase.

The recombinant biocatalyst can be a transformed non-human organism, for example, a microorganism, which contains a heterologous nucleic acid molecule encoding an enzyme which catalyzes at least one step in the desulfurization of thiophene. The recombinant biocatalyst can also be an enzyme preparation derived from such a transformed non-human organism.

The recombinant biocatalyst can be immobilized to facilitate its separation from the reaction mixture. As set forth above, a non-viable microorganism may serve as the carrier for the desulfurization agent.

As set forth above, the thiophene substrate, e.g. a thiophene-containing refined fossil fuel, such as gasoline or naphtha, can be contacted with the recombinant biocatalyst, wherein the recombinant biocatalyst catalyzes the catabolism of the thiophene or substituted thiophenes. In one embodiment, inorganic sulfur, for example sulfate, is produced, and generally, is insoluble or substantially insoluble in the fossil fuel. By "insoluble", is meant that at least a portion of the inorganic sulfur can be removed from the fossil fuel by separation techniques such as extraction, distillation, settling, filtering or centrifugation. The treated substrate, e.g. the fossil fuel, has a reduced sulfur content.

The microorganism can be added to the substrate, e.g. the fossil fuel, in an aqueous phase, which can be water taken alone or in combination with one or more suitable solvents, including oil or organic solvents, miscible or immiscible with water. The choice of solvent is, generally, within the skill in the art. The reaction medium, where it consists of two phases, can form a water-in-oil, or oil-in-water emulsion or microemulsion. In such an embodiment, the organic product of the reaction, generally, is removed from the reaction medium in the organic phase while the inorganic sulfur compound, where produced, is removed in the aqueous phase.

Conditions of the desulfurization process are generally chosen to maximize biocatalytic reaction. For example, where the biocatalytic reaction is oxidative, such as that employing Nocardia sp., the reaction is achieved in the presence of oxygen, such as oxygen gas, air or oxygen-enriched air. The oxygen can be added to the aqueous or oil phase prior to or during the reaction. The temperature and pH also can be manipulated to enhance biocatalytic reaction. For example, preferred temperatures for the desulfurization step are in the range of between about 15° C. and 40° C. The pH can be maintained between about 5 and 9.

The desulfurization and separation steps can be accomplished in a batch, semi-batch or continuous process or combination thereof. A preferred embodiment employs a continuous process. Where a continuous process is performed, the thiophene-containing material or fossil fuel and biocatalyst streams can run co- or countercurrently, preferably countercurrently.

The reaction medium so obtained is then, preferably, incubated or maintained, optionally with agitation, for a sufficient period of time to permit biocatalytic reaction. The term "incubating" is defined as exposing the reaction substrate to the microorganism under conditions suitable for reaction.

As discussed above, several suitable techniques for monitoring the rate and extent of desulfurization are well-known and readily available to those skilled in the art. Baseline and timecourse samples can be collected from the incubation mixture, and prepared for a determination of the residual organic sulfur in the fossil fuel. The disappearance of sulfur from organosulfur compounds, such as 2-methylthiophene and 3-methylthiophene, in the sample being subjected to biocatalyst treatment, can be monitored using, e.g. X-ray fluorescence (XRF) or atomic emission spectrometry.

The desulfurization step preferably employs a minimum volume of the aqueous stream to reduce costs in the water separation. Some microorganisms and enzymes require a small amount of water to maintain viability or an effective configuration. In such instances, the water content is preferably maintained at the lowest concentration practicable, such as that amount sufficient to wet the desulfurization agent. Additional microorganisms may also be added to enhance the biocatalytic reaction. This would be appropriate, for example, where the microorganism of the desulfurization step does not possess the entire profile of enzymes required for the biocatalytic degradation of the sulfur compounds.

By way of specific example, the biochemical pathway of the oxidation of an alkylthiophene to an alkylphenol is likely to occur in at least 2 stages, catalyzed by two or more enzymes. The methods of the present invention can include one or all of these stages.

The invention is further illustrated by the following examples:

EXAMPLES

Example 1

Biotransformation of $^{14}$C-thiophene by KGB1

$^{14}$C-thiophene labeled at the 2 and 5 positions of the thiophene ring (specific activity 4.98 mCi/mmol) was obtained from DuPont NEN (Boston, Mass.). *Nocardia asteroides* KGB1 cells were grown on minimal medium R1 with benzothiophene or sulfate as the sulfur source to a cell $OD_{600}$ of 1.9. The cells were then collected, washed, and resuspended in 50 mM, pH 6.9 phosphate buffer (final cell $OD_{600}$=13). Four microliters of 0.1 M $^{14}$C-thiophene in ethanol was added to 4 ml cells (final concentration of $^{14}$C-thiophene is 100 $\mu$M) and the bottles were sealed immediately. The bottles were shaken at 30° C. and 1 ml samples (cell plus supernatant) were taken at 0 and 22 hr from different bottles. The cells were removed by centrifugation and the supernatants were analyzed by HPLC using a radiometric detector.

Figure 2B:
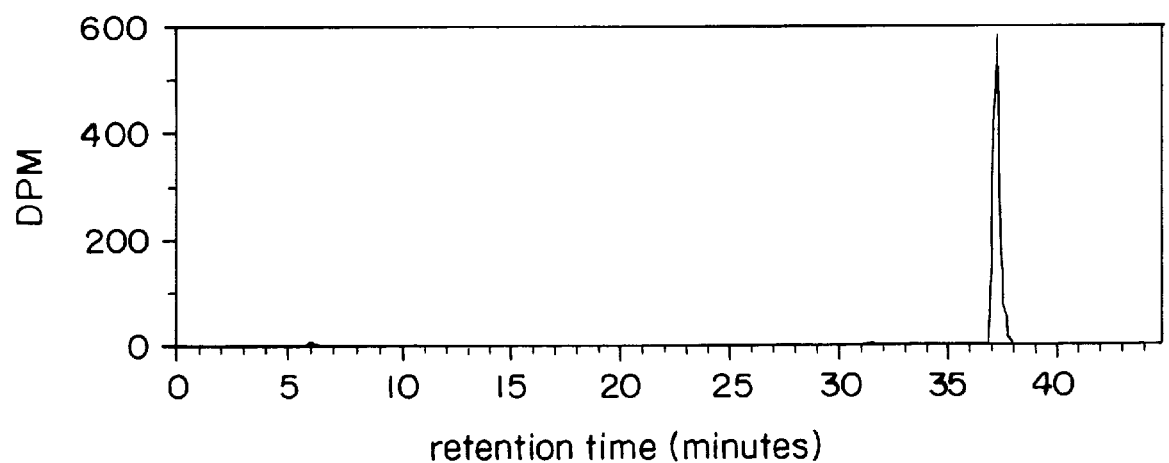
FIG. 2B presents the results of $^{14}$C-thiophene biotransformation by KGB1 cells grown on sulfate-containing medium.

The HPLC (radiometric detection) profiles of the biotransformations are shown in FIGS. 2A and 2B. A major product of $^{14}$C-thiophene biotransformation by KGB1 grown on benzothiophene as sulfur source was detected with a retention time of 6 minutes (FIG. 2A). A small peak with a retention time of 12.5 min was also detected. There is also a much smaller peak with a retention time of 33.5 min. A small amount of $^{14}$C-thiophene (retention time 37 min) was also observed. No products were detected from the biotransformation of $^{14}$C-thiophene by KGB1 grown on sulfate as sulfur source (FIG. 2B). This result demonstrates that strain KGB1 has the ability to transform $^{14}$C-thiophene and that expression of the relevant enzymes is repressed by sulfate.

Example 2

Cloning of the Genes for Desulfurization of Thiophenes from KGB1

Genomic DNA of strain KGB1 was isolated based on the method of Wilson, in Ausubel et al. Current Protocols in Molecular Biology, Wiley-Interscience, New York. This DNA was partially digested by HindIII and the pUC18 based vector pEX92 (Xi, L., J. D. Childs, D. J. Monticello, and C. H. Squires in Flavins and Flavoproteins 403–406 (1996)) was completely digested by HindIII. The DNAs were mixed at the ratio of 20:1 (genomic DNA:vector) and ligated. The ligation mixture was then electroporated into *E. coli* strain DH10B. The cells were plated on LB+Amp+IPTG medium and incubated at 37° C. overnight and then growth continued at room temperature.

Figure 3:
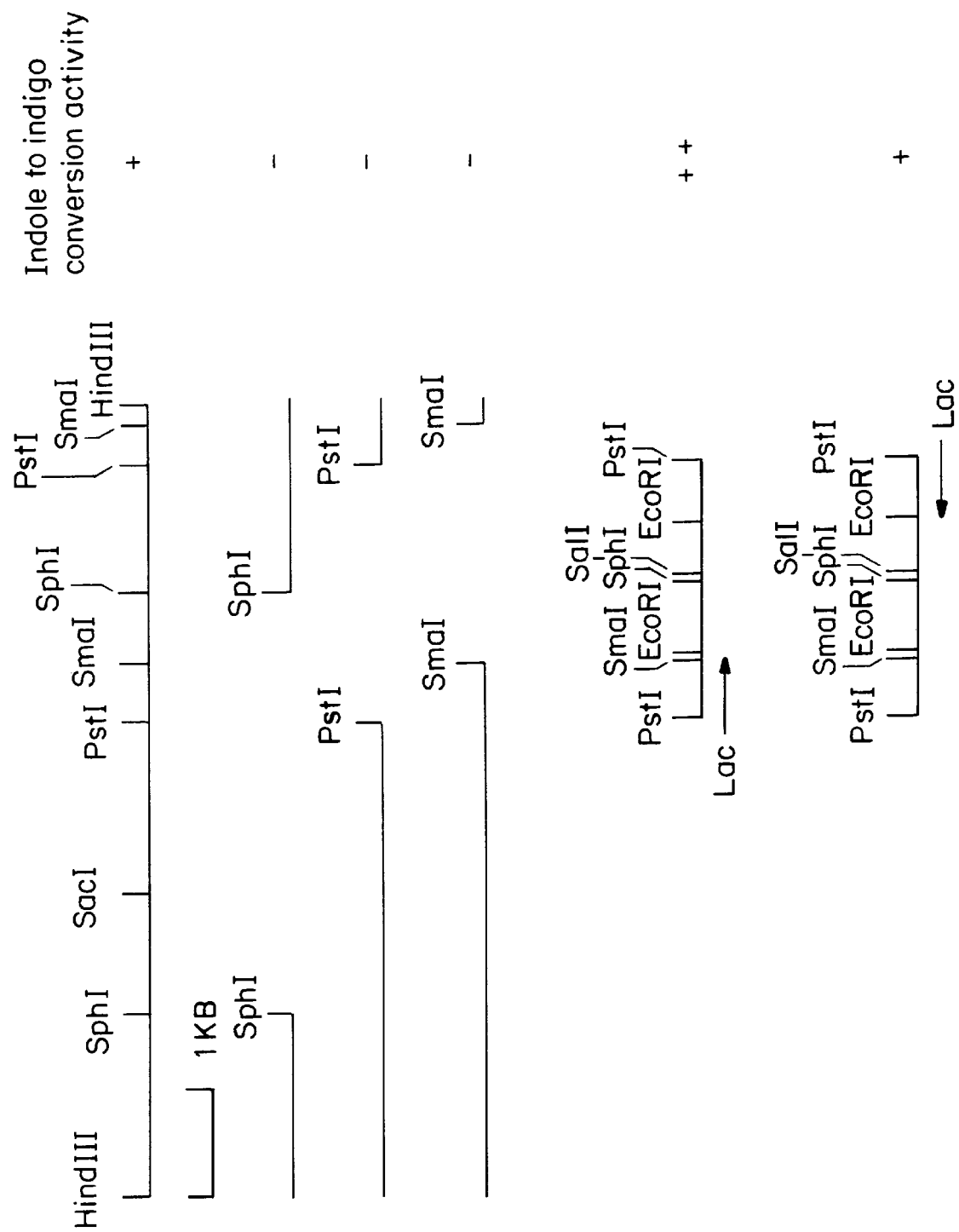
FIG. 3 presents a restriction map and subcloning of the original clone pYZW100.

Most *E. coli* strains grown on a rich medium can utilize tryptophan as a source of carbon and nitrogen through an inducible tryptophanase-tryptophan permease system that converts tryptophan to indole, pyruvate, and ammonia (Snell, E. E., *Adv. Enzymol.* 42: 287–333 (1976)). Indole is converted into indigo only when the *E. coli* cells have been transformed with DNA containing a gene coding for an enzyme able to catalyze the reaction. The production of indigo will make the colony blue. From 20,000 colonies examined, 2 blue colonies were found after 4 days of incubation. It was later found that these two clones had the same DNA insertion, a 7.5 kb HindIII fragment. This clone was named pYZW100. A simple restriction map is shown in FIG. 3. The blue pigment was extracted by chloroform and the spectrum matched that of indigo (data not shown).

Subcloning

Based on the restriction map (FIG. 3), several subclones were constructed through deletion of part of the original fragment. As shown in FIG. 3, none of the deletion clones retained the ability to turn indole into indigo. All the deletions resulted in the loss of DNA between the two PstI sites. This 2.4 kb PstI fragment was therefore cloned into vector pNEB193 (a derivative of pUC19, with more cloning sites) purchased from New England Biolabs. Beverly, Mass. This clone was able to turn indole into indigo in one orientation (named pYZW101) relative to the lac promoter much faster than in the opposite orientation (named pYZW102) based on the rate the colonies turned blue. The direction of the open reading frame was deduced from this result. As will be shown in Example 4, the direction of the ORF matches the prediction.

Example 3

Expression of the Gene and Activity Assay on Biotransformation of Thiophenes

Construction of Expression Clone

As described above, clone pYZW102 was constructed at the same time as the clone pYZW101. The insertion orientation of this clone was opposite to that of pYZW101. A HindIII-XbaI fragment (HindIII and XbaI are cutting sites from the vector pNEB193, not shown in FIG. 3) containing the PstI fragment from this clone was cloned into the expression vector pEBC700. The new construct was named pYZW103 and $E.$ $coli$ strain DH10B was the host for this construct.

Activity Assay on $^{14}C$-thiophene $E.$ $coli$ containing clone pYZW103 was grown in LB medium and induced by 1 mM IPTG. A negative control was performed using cells containing the vector pEBC700 with no insert. Cells were washed and resuspended in phosphate buffer. The final cell $OD_{600}$ was 7.0. 100 $\mu$M $^{14}C$-thiophene was added to 4 ml cells in a sealed bottle. The bottle was shaken at 30° C. for 18 hr. Then 1 ml of sample supernatant was used for HPLC analysis using a radiometric detector.

Figure 4A:
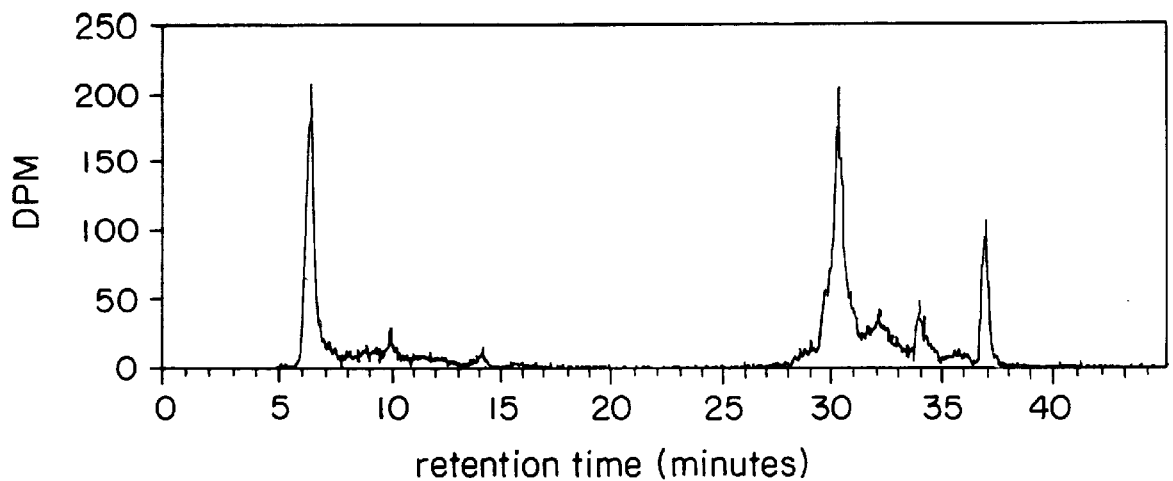
FIG. 4A presents the results of $^{14}$C-thiophene biotransformation by clone pYZW103.
Figure 4B:
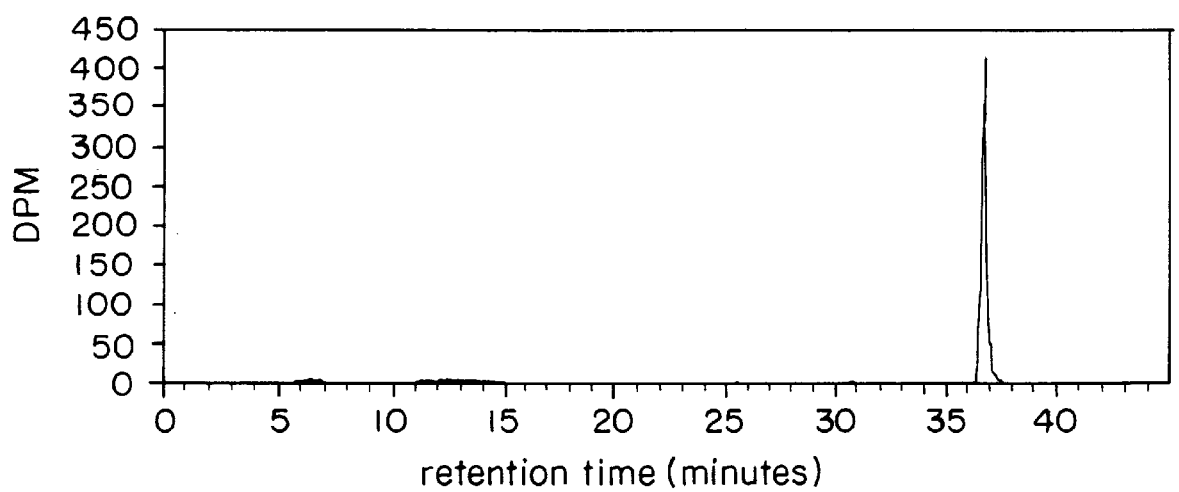
FIG. 4B presents the results of $^{14}$C-thiophene biotransformation by clone pEBC700.

The HPLC results are shown in FIGS. 4A and 4B. Two major products with retention times of 6 minutes and 30.5 minutes, respectively, were detected (FIG. 4A). The negative control showed no product (FIG. 4B). Both $E.$ $coli$ (pYZW103) and wild type KGB1 can transform $^{14}C$-thiophene to a product with a retention time of 6 min.

Figure 5:
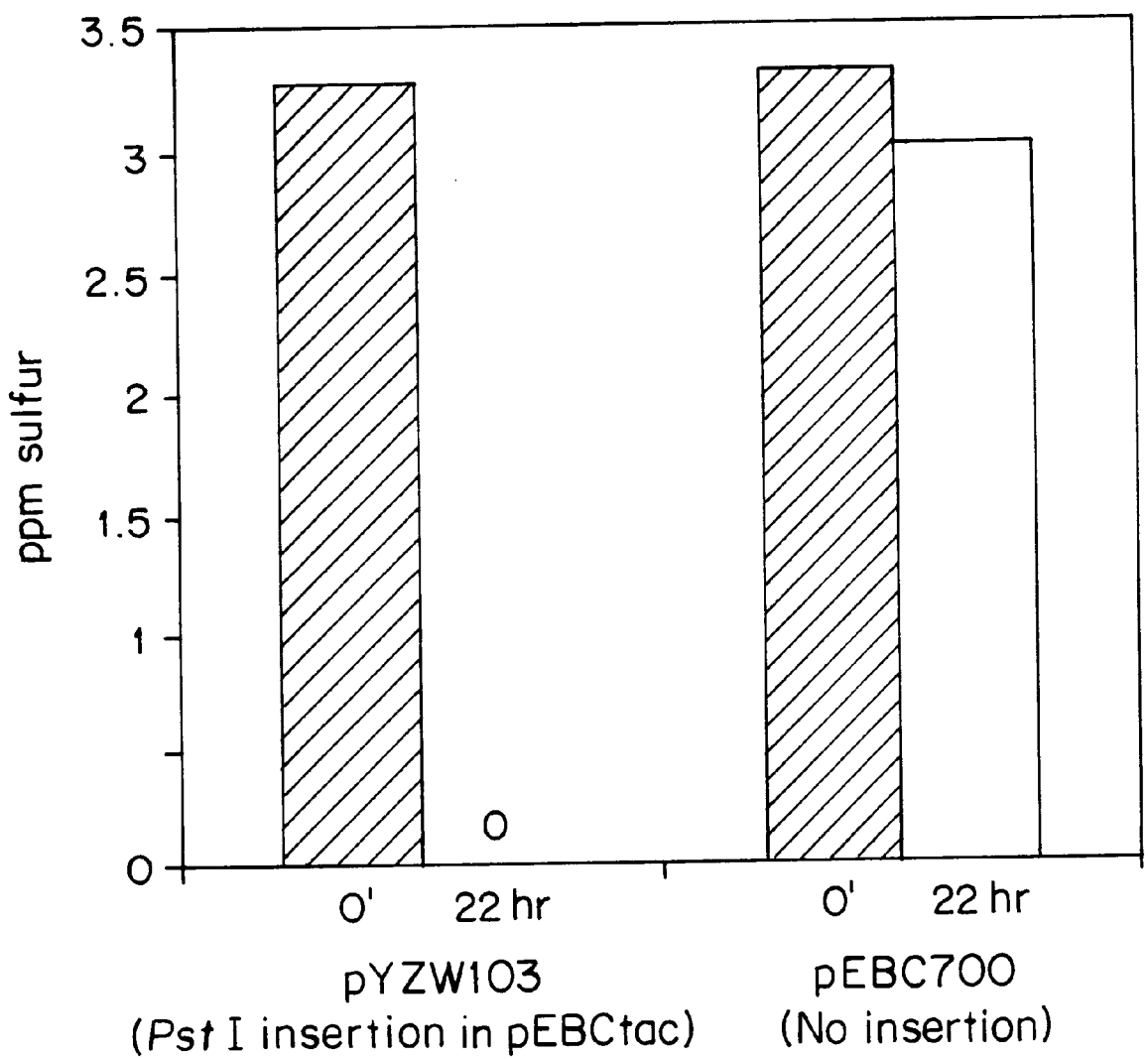
FIG. 5 presents the results of the biotransformation of 3-methyl-thiophene by clone pYZW103.

Activity Assay on 3-Methyl-thiophene $E.$ $coli$ cells were prepared in the same way as described above. 5 $\mu$L of 100 $\mu$M 3-methyl-thiophene in N,N-dimethylformamide was added to 5 ml of cell suspension in a sealed bottle and the bottle was shaken for 22 hours. The contents were then extracted with 5 ml of hexane and the organic layer was analyzed by GC-SCD. As shown in FIG. 5, 3-methyl-thiophene completely disappeared when incubated with $E.$ $coli$ cells containing clone pYZW103, but was unchanged when incubated with the negative control $E.$ $coli$ containing the vector only. This result indicated that the clone pYZW103 had activity on 3-methyl-thiophene.

Functional Analysis of ORF

Figure 6:
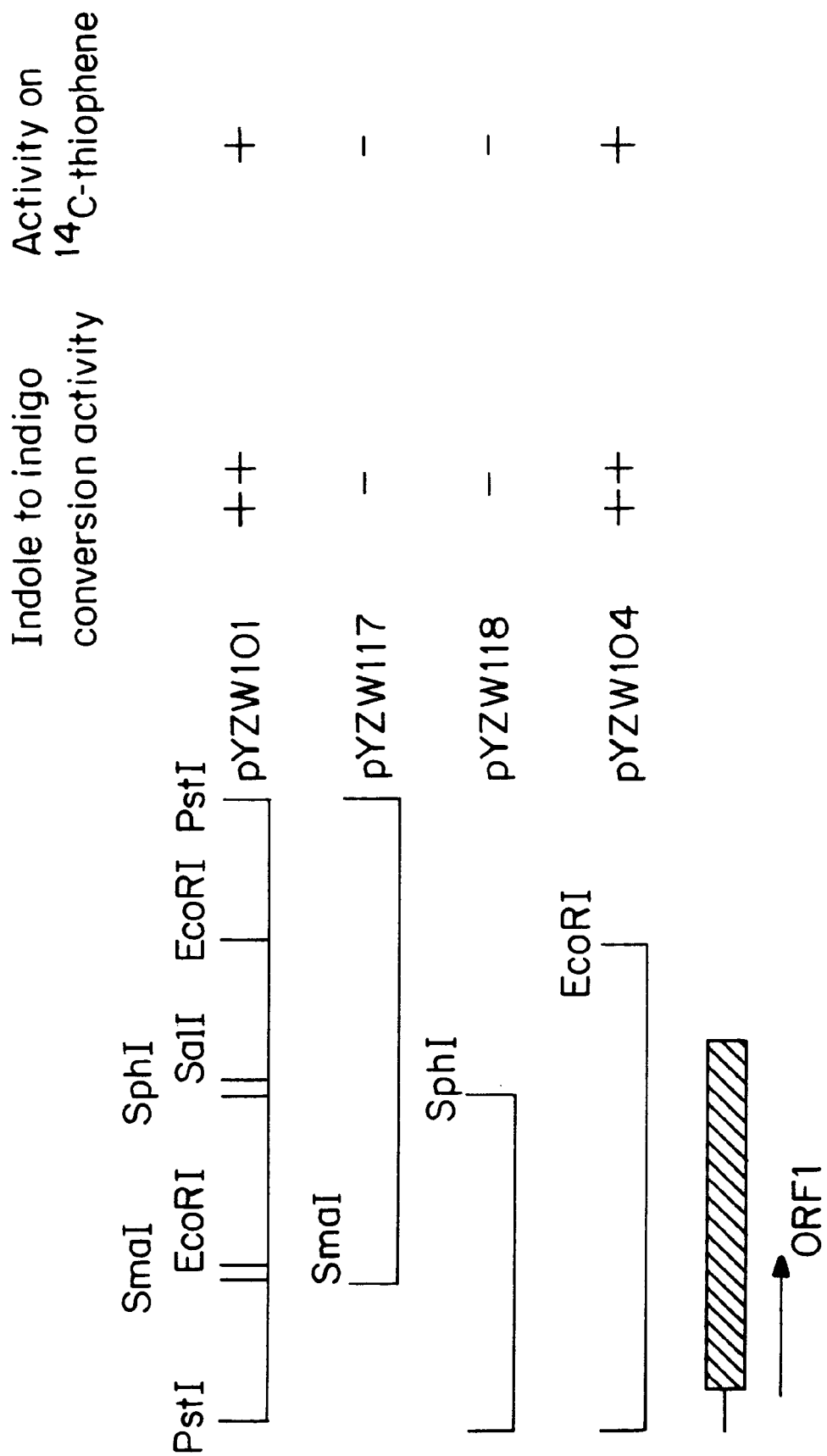
FIG. 6 presents an analysis of the function of ORF.

As is shown in Example 4, an open reading frame was found in the 2.4 kb PstI fragment. In order to analyze the function of this open reading frame, different subclones derived from pYZW101 and pYZW102 (2.4 kb PstI fragment in pNEB193 in two different orientations) were constructed and their activities on indole and $^{14}C$-thiophene were tested. The results are shown in FIG. 6. The clone pYZW117, which contains part of ORF, did not show any activity. The clone pYZW118, which contains only part of ORF also showed no activity. The clone pYZW104, which contains the entire ORF, showed activity. The HPLC profiles of $^{14}C$-thiophene biotransformation by clone pYZW101 and pYZW104 are the same (data not shown). These results indicate that the protein encoded by ORF is sufficient to catalyze the conversions of indole and $^{14}C$-thiophene in $E.$ $coli.$ Example 4

Sequencing of the 2.4 kb PstI Fragment

Sequencing

Sequencing reactions were performed using a Dye Terminator Cycle Sequencing Kit from Perkin Elmer, Foster City, Calif. and the samples were analyzed by Seqwright, Houston, Tex. Both strands of the 2.4 kb PstI fragment were sequenced.

The 2.4 kb PstI fragment includes an open reading frame that includes nucleotides 131 to 1495 and codes for a 455 amino acid protein with a calculated molecular weight of 51,800. The nucleotide sequence and corresponding amino acid sequence of this open reading frame are shown in FIG. 1. The GC content of the sequenced region is 61.2%. ORF shows a very high GC percentage at the third position of the codon, which is evidence that this open reading frame encodes a protein (Bibb, M. J., P. R. Findly, and M. W. Johnson, Gene 30: 157–166 (1984)). A possible ribosome binding site, GAGGA, was found in front of the ATG start codon for ORF.

Sequence Analysis

A FASTA search from the database revealed that the ORF-encoded protein has homology to mammalian dimethylaniline monooxygenases, also named flavin-containing monooxygenases, FMO. No protein from bacteria or other prokaryotic cells was found to have homology to the protein encoded by ORF. FMOs catalyze the oxidation of nucleophilic nitrogen, sulfur, and phosphorus atoms in a wide variety of compounds. A typical reaction is as follows:

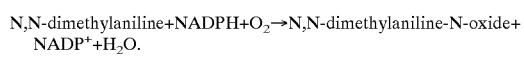

$N,N$-dimethylaniline+NADPH+$O_2$→$N,N$-dimethylaniline-$N$-oxide+ NADP$^+$+H$_2$O.

These enzymes are typically localized in the microsomes in organs such as liver and lung. If the ORF encoded protein is considered to belong to this family, then this is the first gene from this family to be isolated from bacteria. The amino acid sequence alignment (created using the GCG program GAP) of the protein encoded by ORF and one of the FMOs, FMO5 from human (Overby (SEQ ID NO:5) et al., $Arch.$ $Biochem.$ $Biophys$ 317: 275–284 (1995)), is show in FIG. 7. A "|" indicates that the two aligned amino acids are identical. A ":" indicates that the two aligned two amino acids are very similar to each other. A "." indicates that the two aligned two amino acids are similar to each other. The putative pyrophosphate-binding sequences (GxGxxG) are underlined. There is 29.2% identity and 52.9% similarity between the two complete proteins. As reported in the literature, the identities of all known homologous FMO forms are between 52 and 57%. Therefore, the ORF1 encoded protein is distinct from the others. There are a number of gaps (20) in the alignment. The N-terminal and C-terminal portions of the two proteins match each other relatively well. There are huge gaps in the middle part of the alignment. There are two putative pyrophosphate-binding sequences (GxGxxG) in FMO5. In the ORF-encoded protein, only one such sequence is found in the N-terminus (GAGPSG). These are shown as underlined in FIG. 7.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A nucleic acid molecule encoding an enzyme having the amino acid sequence set forth in SEQ ID NO.: 2; or an enzymatically active fragment thereof.

2. The nucleic acid molecule of claim 1 having the sequence set forth in SEQ ID NO.: 1.

3. A nucleotide sequence comprising at least about 20 contiguous nucleotides from the sequence of SEQ ID NO.: 1, or the complement thereof.

4. The nucleotide sequence of claim 3 comprising at least about 40 contiguous nucleotides from the sequence of SEQ ID NO.: 1 or the complement thereof.

5. The nucleotide sequence of claim 4 comprising at least about 50 contiguous nucleotides from the sequence of SEQ ID NO.: 1 or the complement thereof.

6. A plasmid comprising a nucleic acid molecule of claim 1 operatively linked to a promoter.

7. A plasmid comprising a nucleic acid molecule of claim 2 operatively linked to a promoter.

8. A transformed microorganism containing a recombinant DNA plasmid comprising a DNA molecule encoding an enzyme set forth in SEQ ID NO.: 2, or an active fragment thereof.

* * * * *

SEQUENCE LISTING

<160> NUMBER OF SEQ ID NOS: 3

<210> SEQ ID NO: 1
<211> LENGTH: 1365
<212> TYPE: DNA
<213> ORGANISM: Nocardia asteroides

<400> SEQUENCE: 1

| | | | | | | |
|---|---|---|---|---|---|---|
| atgaacagga | gggtagccgt | catcggtgct | ggcccatcgg | gtcttgcgca | attgcgggca | 60 |
| ttccagtctg | cggcgagcaa | aggcgccgac | atcccggaga | tcgtctgctt | cgagaagcag | 120 |
| gccaactggg | gcgggctttg | gaactacacc | tggcgcaccg | gtctggacca | gtatggcgag | 180 |
| ccggtccatg | gctcgatgta | ccgctacctg | tggtcgaacg | gccccaagga | ggggctggag | 240 |
| ttcgccgact | actccttcga | ggagcatttc | ggcaagcaga | tcgcctccta | tccgccgcgc | 300 |
| gcggtcctgt | tcgactacat | cgagggccgc | gtgaacaagg | caggcgtgcg | cgactggatc | 360 |
| cgcttcgaga | acgtcgtgcg | cctggtgacc | tgggacgaga | acaccaggaa | gttcaccgtc | 420 |
| accgtccagg | acctgcccaa | cgaccattgc | tattccgaag | atttcgacaa | tgtgatcgtc | 480 |
| gcctcgggcc | acttctcgac | cccgaacgtt | cccgaattcc | cgggcttcga | ccagttcaac | 540 |
| ggccgcatcc | tgcacgccca | tgacttccgc | gacgcgcgcg | agttcatcgg | caaggacgtg | 600 |
| ctgctcatcg | gcaccagcta | ctcggccgag | gacatcggct | cgcaatgctg | gaaatacggc | 660 |
| gccaactcca | tcaccaactg | ctaccgcacc | aaacccatgg | gctaccactg | gcccgacaac | 720 |
| tgggaagaaa | agccgctgct | ggagaaggtc | cacgtcaaca | ccgccacctt | caaggacggc | 780 |
| tcgaccaagc | agatcgacgc | catcatcctg | tgcaccggct | acaagcacca | tttcccctcc | 840 |
| ctgcccgacg | acctgcgcct | gaggacggcc | aaccgcctgg | cgacggccga | tctctacaag | 900 |
| ggcgtcgcct | atgtccacaa | tccggcgctg | ttctacatcg | gcatgcagga | ccagtggttc | 960 |
| accttcaaca | tgttcgacgc | ccaggcctgg | tgggcgcgcg | acgtgatcct | gggccgcatc | 1020 |
| gccctgcccg | cggcaagca | ggagatggtc | gccgatgtcg | aggcccgcgt | cgccgccgag | 1080 |
| gacgccggca | aggacgacta | cgacgcgatc | cgctatcagg | gcgactacgt | caaggagctg | 1140 |
| atcgccgaga | ccgactatcc | gagcttcgac | gtcgacggcg | ccaacgaagc | cttcttcgag | 1200 |
| tggaagaagc | acaagaagaa | gaacatcatg | gagttccgcc | acaactccta | tcgctcggtc | 1260 |
| atcaccggca | ccatgggccc | gccccaccac | acgccctgga | aggatgccct | cgacgattcg | 1320 |
| ctgcaagcct | atctcggcac | acaggccgca | ccagccgcag | cagaa | | 1365 |

<210> SEQ ID NO: 2
<211> LENGTH: 455
<212> TYPE: PRT
<213> ORGANISM: Nocardia asteroides -continued

```
<400> SEQUENCE: 2

Met Asn Arg Arg Val Ala Val Ile Gly Ala Gly Pro Ser Gly Leu Ala
 1               5                  10                  15

Gln Leu Arg Ala Phe Gln Ser Ala Ala Ser Lys Gly Ala Asp Ile Pro
             20                  25                  30

Glu Ile Val Cys Phe Glu Lys Gln Ala Asn Trp Gly Gly Leu Trp Asn
         35                  40                  45

Tyr Thr Trp Arg Thr Gly Leu Asp Gln Tyr Gly Glu Pro Val His Gly
     50                  55                  60

Ser Met Tyr Arg Tyr Leu Trp Ser Asn Gly Pro Lys Glu Gly Leu Glu
 65                  70                  75                  80

Phe Ala Asp Tyr Ser Phe Glu Glu His Phe Gly Lys Gln Ile Ala Ser
                 85                  90                  95

Tyr Pro Pro Arg Ala Val Leu Phe Asp Tyr Ile Glu Gly Arg Val Asn
             100                 105                 110

Lys Ala Gly Val Arg Asp Trp Ile Arg Phe Glu Asn Val Val Arg Leu
         115                 120                 125

Val Thr Trp Asp Glu Asn Thr Arg Lys Phe Thr Val Thr Val Gln Asp
     130                 135                 140

Leu Pro Asn Asp His Cys Tyr Ser Glu Asp Phe Asp Asn Val Ile Val
145                 150                 155                 160

Ala Ser Gly His Phe Ser Thr Pro Asn Val Pro Glu Phe Pro Gly Phe
                 165                 170                 175

Asp Gln Phe Asn Gly Arg Ile Leu His Ala His Asp Phe Arg Asp Ala
             180                 185                 190

Arg Glu Phe Ile Gly Lys Asp Val Leu Leu Ile Gly Thr Ser Tyr Ser
         195                 200                 205

Ala Glu Asp Ile Gly Ser Gln Cys Trp Lys Tyr Gly Ala Asn Ser Ile
     210                 215                 220

Thr Asn Cys Tyr Arg Thr Lys Pro Met Gly Tyr His Trp Pro Asp Asn
225                 230                 235                 240

Trp Glu Glu Lys Pro Leu Leu Glu Lys Val His Val Asn Thr Ala Thr
                 245                 250                 255

Phe Lys Asp Gly Ser Thr Lys Gln Ile Asp Ala Ile Ile Leu Cys Thr
             260                 265                 270

Gly Tyr Lys His His Phe Pro Phe Leu Pro Asp Asp Leu Arg Leu Arg
         275                 280                 285

Thr Ala Asn Arg Leu Ala Thr Ala Asp Leu Tyr Lys Gly Val Ala Tyr
     290                 295                 300

Val His Asn Pro Ala Leu Phe Tyr Ile Gly Met Gln Asp Gln Trp Phe
305                 310                 315                 320

Thr Phe Asn Met Phe Asp Ala Gln Ala Trp Trp Ala Arg Asp Val Ile
                 325                 330                 335

Leu Gly Arg Ile Ala Leu Pro Ala Gly Lys Gln Glu Met Val Ala Asp
             340                 345                 350

Val Glu Ala Arg Val Ala Ala Glu Asp Ala Gly Lys Asp Tyr Asp
         355                 360                 365

Ala Ile Arg Tyr Gln Gly Asp Tyr Val Lys Glu Leu Ile Ala Glu Thr
     370                 375                 380

Asp Tyr Pro Ser Phe Asp Val Asp Gly Ala Asn Glu Ala Phe Phe Glu
385                 390                 395                 400

Trp Lys Lys His Lys Lys Asn Ile Met Glu Phe Arg His Asn Ser
                 405                 410                 415
```

-continued

Tyr Arg Ser Val Ile Thr Gly Thr Met Gly Pro Pro His His Thr Pro
            420                 425                 430

Trp Lys Asp Ala Leu Asp Asp Ser Leu Gln Ala Tyr Leu Gly Thr Gln
            435                 440                 445

Ala Ala Pro Ala Ala Ala Glu
            450                 455

<210> SEQ ID NO: 3
<211> LENGTH: 520
<212> TYPE: PRT
<213> ORGANISM: Homo sapien

<400> SEQUENCE: 3

Thr Lys Lys Arg Ile Ala Val Ile Gly Gly Gly Val Ser Gly Leu Ser
  1               5                  10                  15

Ser Ile Lys Cys Cys Val Glu Glu Gly Leu Glu Pro Val Cys Phe Glu
                 20                  25                  30

Arg Thr Asp Asp Ile Gly Gly Leu Trp Arg Phe Gln Glu Asn Pro Glu
             35                  40                  45

Glu Gly Arg Ala Ser Ile Tyr Lys Ser Val Ile Ile Asn Thr Ser Lys
         50                  55                  60

Glu Met Met Cys Phe Ser Asp Tyr Pro Ile Pro Asp His Tyr Pro Asn
 65                  70                  75                  80

Phe Met His Asn Ala Gln Val Leu Glu Tyr Phe Arg Met Tyr Ala Lys
                 85                  90                  95

Glu Phe Asp Leu Leu Lys Tyr Ile Arg Phe Lys Thr Thr Val Cys Ser
                100                 105                 110

Val Lys Lys Gln Pro Asp Phe Ala Thr Ser Gly Gln Trp Glu Val Val
            115                 120                 125

Thr Glu Ser Glu Gly Lys Lys Glu Met Asn Val Phe Asp Gly Val Met
        130                 135                 140

Val Cys Thr Gly His His Thr Asn Ala His Leu Pro Leu Glu Ser Phe
145                 150                 155                 160

Pro Gly Ile Glu Lys Phe Lys Gly Gln Tyr Phe His Ser Arg Asp Tyr
                165                 170                 175

Lys Asn Pro Glu Gly Phe Thr Gly Lys Arg Val Ile Ile Ile Gly Ile
            180                 185                 190

Gly Asn Ser Gly Gly Asp Leu Ala Val Glu Ile Ser Gln Thr Ala Lys
        195                 200                 205

Gln Val Phe Leu Ser Thr Arg Arg Gly Ala Trp Ile Leu Asn Arg Val
    210                 215                 220

Gly Asp Tyr Gly Tyr Pro Ala Asp Val Leu Phe Ser Ser Arg Leu Thr
225                 230                 235                 240

His Phe Ile Trp Lys Ile Cys Gly Gln Ser Leu Ala Asn Lys Tyr Leu
                245                 250                 255

Glu Lys Lys Ile Asn Gln Arg Phe Asp His Glu Met Phe Gly Leu Lys
            260                 265                 270

Pro Lys His Arg Ala Leu Ser Gln His Pro Thr Leu Asn Asp Asp Leu
        275                 280                 285

Pro Asn Arg Ile Ile Ser Gly Leu Val Lys Val Lys Gly Asn Val Lys
    290                 295                 300

Glu Phe Thr Glu Thr Ala Ala Ile Phe Glu Asp Gly Ser Arg Glu Asp
305                 310                 315                 320

Asp Ile Asp Ala Val Ile Phe Ala Thr Gly Tyr Ser Phe Asp Phe Pro

-continued

```
                        325                 330                 335
Phe Leu Glu Asp Ser Val Lys Val Val Lys Asn Lys Ile Ser Leu Tyr
            340                 345             350

Lys Lys Val Phe Pro Pro Asn Leu Glu Arg Pro Thr Leu Ala Ile Ile
        355                 360             365

Gly Leu Ile Gln Pro Leu Gly Ala Ile Met Pro Ile Ser Glu Leu Gln
    370                 375             380

Gly Arg Trp Ala Thr Gln Val Phe Lys Gly Leu Lys Thr Leu Pro Ser
385             390                 395             400

Gln Ser Glu Met Met Ala Glu Ile Ser Lys Ala Gln Glu Glu Ile Asp
                405             410             415

Lys Arg Tyr Val Glu Ser Gln Arg His Thr Ile Gln Gly Asp Tyr Ile
            420             425             430

Asp Thr Met Glu Glu Leu Ala Asp Leu Val Gly Val Arg Pro Asn Leu
            435             440             445

Leu Ser Leu Ala Phe Thr Asp Pro Lys Leu Ala Leu His Leu Leu Leu
    450             455             460

Gly Pro Cys Thr Pro Ile His Tyr Arg Val Gln Gly Pro Gly Lys Trp
465             470             475             480

Asp Gly Ala Arg Lys Ala Ile Leu Thr Thr Asp Asp Arg Ile Arg Lys
            485             490             495

Pro Leu Met Thr Arg Val Val Glu Arg Ser Ser Ser Met Thr Ser Thr
            500             505             510

Met Thr Ile Gly Lys Phe Met Leu
            515             520
```